United States Patent
Morris et al.

[11] Patent Number: 5,848,691
[45] Date of Patent: Dec. 15, 1998

[54] PACKAGE FOR SPHINCTEROTOME OR CATHETER INCLUDING STRUCTURE MAINTAINING SHAPE OF DISTAL TIP

[75] Inventors: Eugene C. Morris, Winston-Salem; Mark C. Martel, Belews Creek, both of N.C.

[73] Assignee: Wilson-Cook Medical Inc., Winston-Salem, N.C.

[21] Appl. No.: 888,882

[22] Filed: Jul. 7, 1997

[51] Int. Cl.⁶ ..................................................... B65D 83/10
[52] U.S. Cl. ........................... 206/364; 206/438; 206/564
[58] Field of Search .................................... 206/363–365, 206/438, 439, 562–565; 604/280, 281

[56] References Cited

U.S. PATENT DOCUMENTS

| | | |
|---|---|---|
| Re. 29,343 | 8/1977 | Amplatz . |
| 3,633,758 | 1/1972 | Morse et al. . |
| 4,262,800 | 4/1981 | Nethercutt ............................... 206/364 |
| 4,779,727 | 10/1988 | Taterka et al. . |
| 4,850,954 | 7/1989 | Charvin ................................... 206/438 |
| 4,923,061 | 5/1990 | Trombley, III . |
| 4,925,448 | 5/1990 | Bazaral . |
| 5,105,942 | 4/1992 | van Veen et al. . |
| 5,131,537 | 7/1992 | Gonzales . |
| 5,165,540 | 11/1992 | Forney . |
| 5,205,830 | 4/1993 | Dassa et al. . |
| 5,295,493 | 3/1994 | Radisch, Jr. . |
| 5,322,163 | 6/1994 | Foos . |
| 5,372,254 | 12/1994 | Gross ....................................... 206/364 |
| 5,383,849 | 1/1995 | Johlin, Jr. . |
| 5,497,601 | 3/1996 | Gonzalez . |
| 5,526,928 | 6/1996 | Yabe et al. ............................... 206/364 |
| 5,549,563 | 8/1996 | Kronner . |
| 5,568,865 | 10/1996 | Mase et al. ............................... 206/363 |

*Primary Examiner*—Paul T. Sewell
*Assistant Examiner*—Luan K. Bui
*Attorney, Agent, or Firm*—Richard J. Godlewski

[57] ABSTRACT

A package 10 for maintaining the predetermined desired non-planar, three-dimensional shape of the distal tip 14 of a flexible catheter, cannula, sphincterotome or the like 12 includes a non-relaxing mounting tray 18 with a non-planar, three-dimensional structure 20 restricting movement of the distal tip 14, and a non-relaxing cover 26 detachably secured to the tray 18, trapping part and only part of the distal tip 14 against the three-dimensional structure 20 of the tray 18. The package 10 also includes a particularly configured non-relaxing insert 38 removably received in a bore 16 in the distal tip 14. The tray 18, cover 26 and insert 38 together support the distal tip 14 throughout its entire length. The structure 20 of the tray 18 includes a ramped, relatively tightly arced groove 24 on which the distal tip 14 lies. The cover 26 lies over at least the ramped, arced groove 24 and includes a pair of notches 30 receiving the distal tip 14 therethrough. When the cover 26 is detached from the tray 18, at least the distal tip 14 can be freely perpendicularly withdrawn from the tray 18. The package is particularly useful for maintaining the distal tip 14 in a shape particularly adapted for the performance of a sphincterotomy. The package 12 prevents the relaxation or change of the predetermined desired non-planar, three-dimensional shape of the distal tip 14 of the catheter, cannula, sphincterotome or the like 12 during sterilization and storage. The insert 38 and the combination of the tray 18 and the cover 26 are separately useful for this purpose.

18 Claims, 5 Drawing Sheets

PACKAGE FOR SPHINCTEROTOME OR CATHETER INCLUDING STRUCTURE MAINTAINING SHAPE OF DISTAL TIP

TECHNICAL FIELD

This invention relates generally to medical devices, and more particularly to a package for a sphincterotome, a catheter or the like having a distal tip with a predetermined desired non-planar, three-dimensional shape.

BACKGROUND OF THE INVENTION

A wide variety of elongated and generally hollow devices can introduced into the body for a variety of purposes. These purposes include the supply of therapeutic fluids, the implantation of other therapeutic devices, and the introduction of operative instruments, among others. Catheters, cannulae, papillotomes and sphincterotomes are just some of the many examples of such devices. The sphincterotome and the papillotome in particular are well-known devices useful for performing surgical cutting at a site inside a patient. In an endoscopic sphincterotomy, for example, an electrosurgical tool such as a sphincterotome or a papillotome is employed with an endoscope to cut the tissue forming a sphincter within a patient. One sphincter commonly cut by endoscopic sphincterotomy is the sphincter of Oddi, which is formed in the papilla of Vater and which opens into the duodenum. The sphincter of Oddi communicates with the ampulla of Vater, the common channel into which the biliary duct (the common bile duct) and the pancreatic duct merge. Such a sphincterotomy entails the use of a papillotome to cut open the papilla of Vater and allow the performance of other treatments. Typical of these treatments is the removal of gallstones obstructing the biliary duct.

A very useful sphincterotome (a papillotome) and surgical methods of its use are disclosed in U.S. Pat. No. 5,024,617 (J. Karpiel, Jun. 18, 1991). The specification of the patent notes that a survey conducted by the American Society for Gastrointestinal Endoscopy revealed that the most common major complication from endoscopic sphincterotomy was bleeding. The specification of the patent also notes that the vast majority of such bleeding typically results when the retroduodenal artery is cut. Other major complications include pancreatitis, perforation and cholangitis. Indeed, U.S. Pat. No. 5,383,849 (F. Johlin, Jr., Jan. 24, 1995) notes that, when a cannula is used in endoscopic retrograde cholangiopancreatography (ERCP), difficulty is sometimes encountered in the attempt to successfully cannulate the desired duct among the bile and pancreatic ducts. That particular patent discloses a selective cannulator having a distal tip portion which can be oriented in a 10 o'clock or 2 o'clock position relative to the longitudinal axis of the intermediate straight portion of the cannulator.

Other catheters, cannulae, sphincterotomes and the like are manufactured with distal tip portions with other desired shapes, particularly suited to their ultimate functions. Unfortunately, it is often the case that the overall shapes of such catheters, cannulae, sphincterotomes and the like will change during the subsequent sterilization process and during storage after manufacture. For example, during the ethylene gas sterilization of several catheters, the long shaft section of the catheters will often increase in length, while the preformed shapes of their distal tips will often relax. As another example, many catheters are formed from a urethane material and are sterilized after manufacture and packaging by a procedure which includes the application of heat. The elevated temperature during sterilization causes the urethane material to relax from its desired curved shape to a more straightened configuration. With both gas and heat sterilization, however, the amount of change in shape or length caused by the sterilization process or encountered during storage will vary between each individual catheter, so that it is impractical to attempt to shape the catheter during the manufacturing process to account for any subsequent change in length or shape caused by sterilization or storage. Moreover, when urethane materials are employed, the curved tip of a catheter tends to straighten out somewhat over time, even when the catheter is stored at ambient temperatures.

U.S. Pat. No. 5,165,540 (L. Forney, Nov. 24, 1992) incidentally notes that one approach to maintaining the desired shape of an angiographic catheter during sterilization or storage is to insert a bendable, nonresilient wire through the center of a section of catheter tubing. A physician or technician then physically bends the wire and catheter combination into the desired shape prior to sterilization. The patent also notes that the additional cost and time required by this approach makes it commercially unacceptable.

A number of other devices are known for attempting to maintain the shape of, or maintain the shape of the tip of, a catheter, cannula, sphincterotome or the like during sterilization and/or storage. Many such devices involve the relatively loose encasement of the curved distal tip in a compartment on a tray. Others involve the placement of the curved distal tip in a groove formed in a flat tray, retained in the groove by small, rounded projections extending from the wall of the groove. Still others involve the insertion of the distal tip through a plurality of guides mounted to a flat tray. None of these packagings supports the distal tips of their respective catheters, cannulae, sphincterotomes or the like throughout the entire lengths of those distal tips. Moreover, none these packagings is particularly adapted to preserve the shape of the distal tip of a catheter, cannula, sphincterotome or the like which has a non-planar, three-dimensional shape. Further, few if any of these packagings permits the free perpendicular withdrawal of the particularly shaped distal tip of a catheter, cannula, sphincterotome or the like from a tray on which it is carried; instead, the distal tip is stretched and thereby altered in shape during such withdrawal.

It should thus be clear that it would be highly desirable to have a package for a flexible catheter, cannula, sphincterotome or the like which prevents the relaxation or change of the non-planar, three-dimensional shape of the distal tip of the catheter, cannula, sphincterotome or the like during sterilization and storage. It should also be clear that it would be highly desirable to have such a package which supports the non-planar, three-dimensional distal tip of a catheter, cannula, sphincterotome or the like throughout the entire length of that distal tip. It would further be desirable to have such a package which permits the perpendicular withdrawal of at least the distal tip of the catheter, cannula, sphincterotome or the like without stretching it.

SUMMARY OF THE INVENTION

The foregoing problems are solved and a technical advance is achieved in a package for a flexible catheter, cannula, sphincterotome or the like. Applicants have discovered a package for any of these which prevents relaxation of the predetermined desired non-planar, three-dimensional shape of their distal tip during sterilization and storage. The package of the present invention comprises a mounting tray, and a non-relaxing cover secured to the tray which retains the distal tip generally against the tray.

More particularly, Applicants employ a cover which traps part and only part of such a distal tip against the mounting tray. The cover and mounting tray support the non-planar, three-dimensional distal tip throughout its entire length. This prevents relaxation of the distal tip and ensures that the predetermined desired non-planar, three-dimensional shape of the distal tip does not change during sterilization and/or storage. The cover employed by Applicants allows the elimination of the small, rounded projections previously needed to maintain prior planar distal tips in a groove in a tray. The elimination of such groove projections allows the distal tip of the catheter, cannula, sphincterotome or the like to be perpendicularly withdrawn from the tray in the present invention without stretching or changing the shape of the distal tip.

Applicants have also discovered a particularly shaped insert useful by itself or with other packaging to maintain the distal tip of a sphincterotome in a shape particularly useful for the introduction of the tip into a patient and the advancement of the distal tip to, and the cannulation of, the sphincter of Oddi.

In a first aspect, then, the present invention is directed to a package for use in conjunction with a flexible sphincterotome or catheter having a distal tip with a predetermined desired non-planar, three-dimensional shape, the package preventing relaxation of the distal tip of the sphincterotome or catheter from its predetermined desired non-planar, three-dimensional shape. The package comprises a generally rigid, non-relaxing mounting tray with a non-planar, three-dimensional structure restricting movement of at least the distal tip of the sphincterotome or catheter, and a generally rigid, non-relaxing cover detachably secured to the tray, trapping part and only part of the distal tip of the sphincterotome or catheter against the non-planar, three-dimensional structure of the tray, a portion of the distal tip of the sphincterotome or catheter lying over the cover opposite the tray; wherein the tray and cover together support the distal tip of the sphincterotome or catheter throughout its entire length.

The tray and the cover are preferably composed of a transparent, plastic material. The tray, cover and sphincterotome or catheter can be contained in an outer wrapper comprising a gas-permeable backing positioned adjacent to the tray, and a transparent polymeric sheet positioned adjacent to the tray opposite the backing. The polymeric sheet can be affixed to the backing in a conventional manner, for example, by heat-sealing or bonding.

The non-planar, three-dimensional structure of the tray preferably comprises a relatively tight arced, ramped groove on which the distal tip of the sphincterotome or catheter lies. The cover lies over the arced, ramped groove, and includes a pair of notches receiving the distal tip of the sphincterotome or catheter therethrough. The portion of the distal tip lying over the cover thus extends between the notches in the cover. The cover and tray are secured to one another in any convenient manner, for example, by one or more pairs of mating cylindrical tabs and recesses formed in them. The use of such a cover in the present invention permits the elimination of the previously required small, rounded projections formed in the grooves of prior trays, thereby allowing at least the distal tip of the sphincterotome or catheter, and preferably the entire sphincterotome or catheter, to be freely perpendicularly withdrawn from the tray when the cover is detached from the tray.

The package of the present invention preferably further comprises a generally rigid, non-relaxing insert removably received in a bore defined in the distal tip of the sphincterotome or catheter. The insert is configured to the predetermined desired non-planar, three-dimensional shape of the distal tip of the sphincterotome or catheter. It is particularly preferred that the three-dimensional structure of the tray, the cover and the insert maintain the distal tip in a shape particularly adapted for the performance of a sphincterotomy. The verbal description of the shape of the insert is problematic; accordingly, it is especially preferred that the three-dimensional structure of the tray, the cover and the insert maintain the distal tip of the sphincterotome or catheter in substantially the shape shown in the Figures.

In a second aspect, the present invention is directed to a package for use in conjunction with a flexible sphincterotome having a distal tip with a predetermined desired non-planar, three-dimensional shape, the distal tip of the sphincterotome including a bore defined therein, and the package preventing relaxation of the distal tip of the sphincterotome from its predetermined desired non-planar, three-dimensional shape. The package of this second aspect comprises a generally rigid, non-relaxing mounting tray with a non-planar, three-dimensional structure restricting movement of at least the distal tip of the sphincterotome; a generally rigid, non-relaxing cover detachably secured to the tray, trapping part and only part of the distal tip of the sphincterotome against the non-planar, three-dimensional structure of the tray, a portion of the distal tip of the sphincterotome lying over the cover opposite the tray; and a generally rigid, non-relaxing insert removably received in the bore of the distal tip of the sphincterotome, the insert being configured to the predetermined desired non-planar, three-dimensional shape of the distal tip of the sphincterotome; wherein the tray and cover together support the distal tip of the sphincterotome throughout its entire length; wherein the non-planar, three-dimensional structure of the tray comprises a ramped, relatively tightly arced groove on which the distal tip of the sphincterotome lies; wherein the cover lies over at least the ramped, arced groove of the tray; wherein the cover includes a pair of notches receiving the distal tip of the sphincterotome therethrough, the portion of the distal tip of the sphincterotome lying over the cover extending between the notches; wherein when the cover is detached from the tray, the at least the distal tip of the sphincterotome can be freely perpendicularly withdrawn from the tray; and wherein the three-dimensional structure of the tray, the cover and the insert maintain the distal tip of the sphincterotome in a shape particularly adapted for the performance of a sphincterotomy.

In a final aspect, the present invention is directed to a generally rigid, non-relaxing insert as described above, removably received in a bore in the distal tip of a sphincterotome which by itself is capable of maintaining the distal tip of the sphincterotome in a shape particularly adapted for the performance of a sphincterotomy. It is preferred that the insert have a shape particularly adapted to maintain the distal tip of the sphincterotome in a 10–12 o'clock position (preferably 11 o'clock), and especially preferred that the insert be shaped substantially as shown in the Figures.

The present invention is particularly advantageous in that it provides a package for a flexible catheter, cannula, sphincterotome or the like which prevents the relaxation or change of the predetermined desired non-planar, three-dimensional shape of the distal tip of the catheter, cannula, sphincterotome or the like during sterilization and storage. The present invention is also advantageous in that it provides support to the predetermined desired non-planar, three-dimensional distal tip of a catheter, cannula, sphincterotome or the like throughout the entire length of that distal tip. The present invention is further advantageous in that it permits the perpendicular withdrawal of at least the distal tip of the catheter, cannula, sphincterotome or the like from the mounting tray without stretching that distal tip.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which:

FIG. 4A top view of a portion of the preferred embodiment of the present invention;

DETAILED DESCRIPTION

Figure 1:
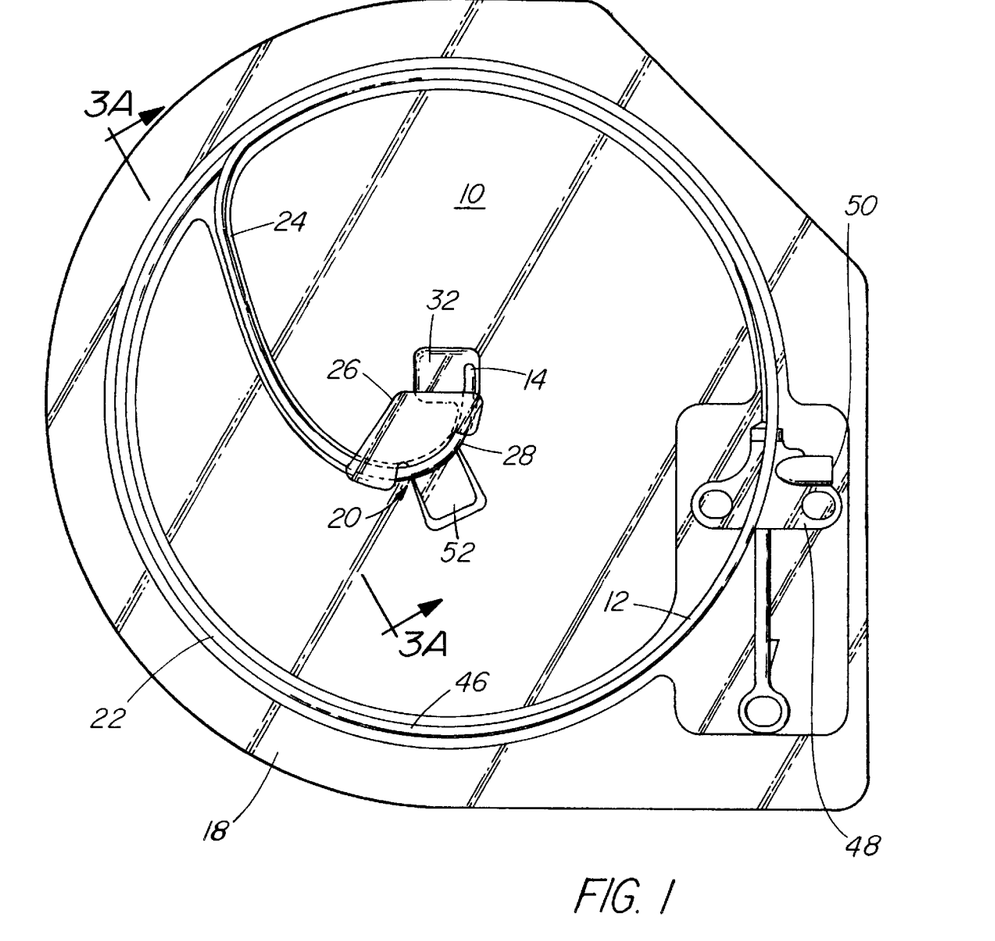
FIG. 1 a to view of the preferred embodiment of the present invention.

With reference first to FIG. 1, a package 10 for use in conjunction with a flexible medical device such as a catheter, cannula, sphincterotome, papillotome or the like is there shown. The medical device is exemplified, without limitation, by a sphincterotome 12. The sphincterotome 12 has a distal tip 14 with a predetermined desired non-planar, three-dimensional shape. The distal tip 14 of the sphincterotome 12 is preferably shaped to facilitate introduction of the sphincterotome 12 through the body and into engagement with a sphincter in the body, for example, into engagement with the sphincter of Oddi. This preferred shape is merely a single example of a variety of predetermined desired non-planar, three-dimensional shapes for the distal tips of flexible catheters, cannulae, sphincterotomes, papillotomes and the like, however. What is important is that, without regard to the particular shape of the medical device or its distal tip, the package 10 prevents its relaxation from its predetermined desired non-planar, three-dimensional shape during sterilization and/or storage of the device.

The sphincterotome 12 or the like preferably includes a bore 16 (more clearly shown in FIG. 6) formed in and extending through at least the distal tip 14 of the sphincterotome 12. The bore 16 may extend through the proximal balance 46 of the sphincterotome 12, if it would facilitate the particular use contemplated for the sphincterotome 12. Preferably, the sphincterotome 12 further includes a conductive wire (not shown) which can be exposed for the electrical cutting of tissue by actuation of a handle 48 located opposite the distal tip 14. Actuation of the handle 48 curves the distal tip 14 of the sphincterotome 12 to an ultimately desired operative position, for example, to a 10 o'clock position with respect to the balance 46 of the sphincterotome 12. A terminal 50 is provided on the sphincterotome handle 48 for supplying a current to the conductive wire. The construction and operation of sphincterotomes and the like are wellknown to those skilled in this art, and no further description of such operation is needed here.

With continued reference to FIG. 1, the package 10 of the present invention first comprises a generally rigid, non-relaxing mounting tray 18 carrying the sphincterotome 12 thereon. The mounting tray 18 includes a non-planar, three-dimensional structure 20 which restricts movement of at least the distal tip 14 of the sphincterotome 12. The package 10 of the present invention also comprises a generally rigid, non-relaxing cover 26 detachably secured to the tray 18. The cover 26 traps part and only part of the distal tip 14 of the sphincterotome 12 against the three-dimensional structure 20 of the mounting tray 18. A portion 28 of the distal tip 14 of the sphincterotome 12 thus lies over the cover 26, opposite the tray 18. The mounting tray 18 and the cover 26 together support the distal tip 14 of the sphincterotome 12 throughout its entire length.

The mounting tray 18 and the cover 26 are preferably but not necessarily composed of the same material. They can conveniently be composed of a medical grade transparent plastic, but a variety of known materials may instead be employed. What is important is that the material of the tray 18 and the cover 26 be more rigid than the material of the distal tip 14 of the sphincterotome 12, and be self-sustaining in shape when subjected to the conditions of sterilization and storage to which the sphincterotome 12 will be subjected. PETG (glycol-modified polyethylene terephthalate), PVC (polyvinyl chloride) and polystyrene are convenient for this purpose.

Figure 2:
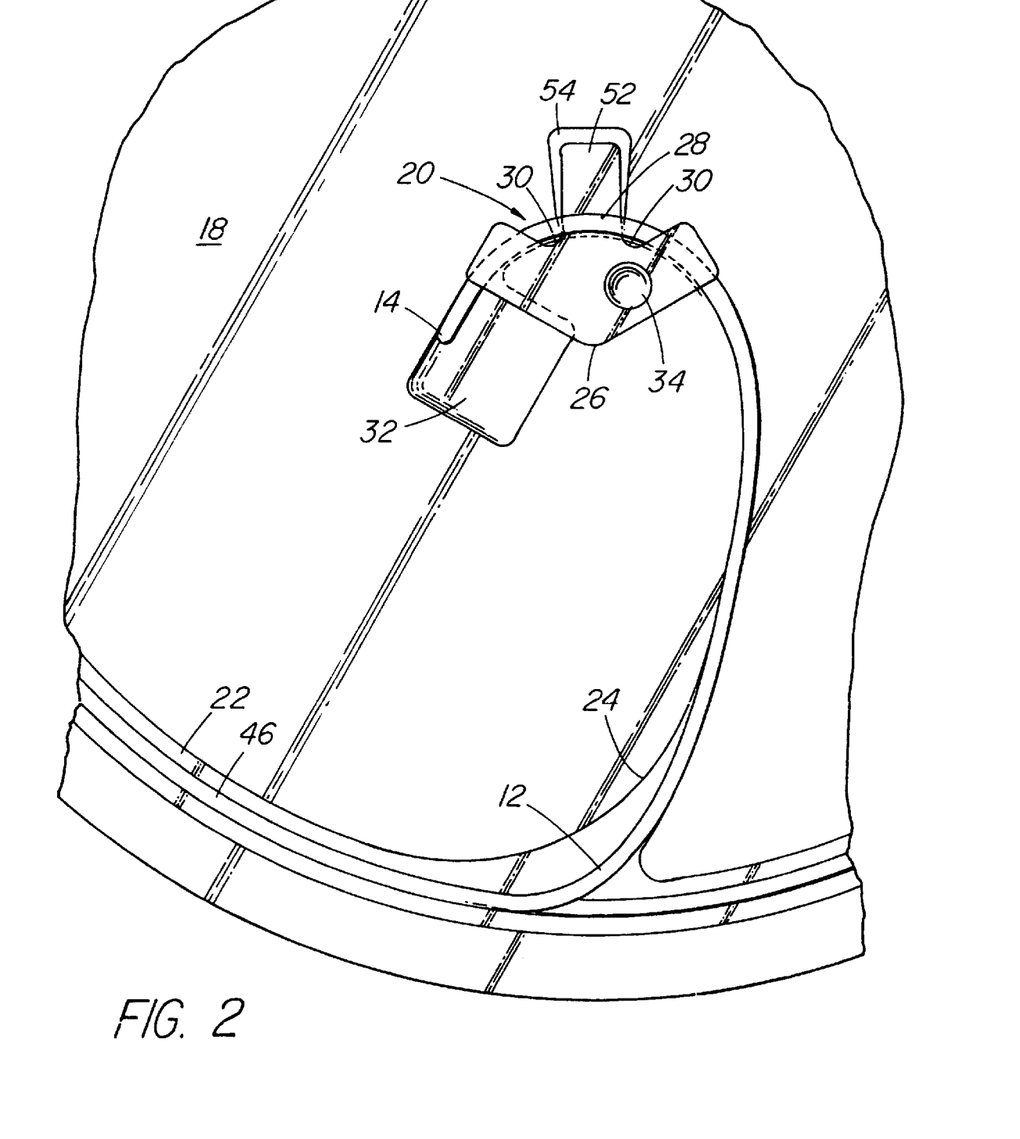
FIG. 2 a top view of a portion of the preferred embodiment of the present invention.
Figure 3A:
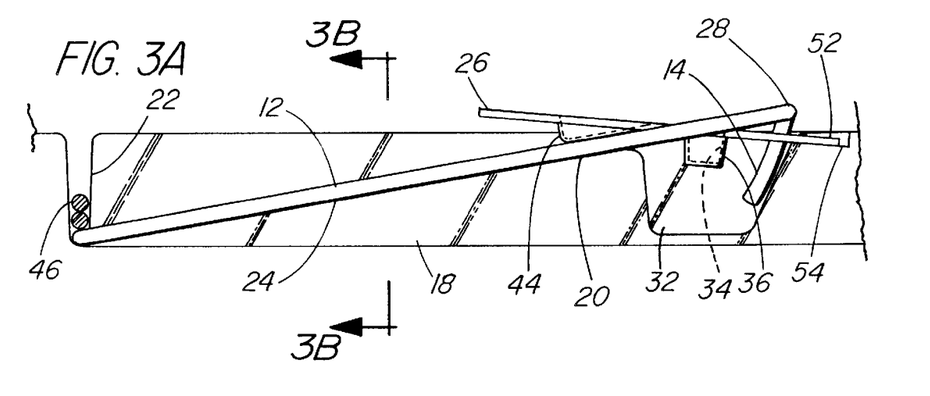
FIG. 3A is a cross-sectional view taken along line 3A—3A of FIG. 1.
Figure 3B:
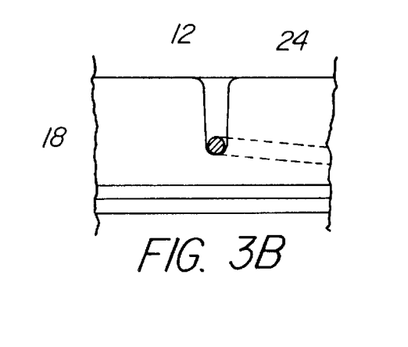
FIG. 3B is a cross-sectional view taken along line 3B—3B of FIG. 3A.

As more clearly shown in the more detailed view of FIG. 2, and in FIGS. 3A and 3B, the non-planar, three dimensional structure 20 of the mounting tray 18 first comprises a relatively tightly arced and ramped groove 24 on which the distal tip 14 of the sphincterotome 12 lies. The cover 26 lies over at least part of the arced and ramped groove 24 of the mounting tray 18. The arced and ramped groove 24 runs substantially the length of the distal tip 14 of the sphincterotome 12, and positions the distal tip 14 significantly out of the plane of the balance 46 of the sphincterotome 12, and orients the distal tip 14 significantly with respect to the plane of the mounting tray 18. The tray 18 further comprises a circular, essentially planar groove 22 positioned about the arced and ramped groove 24, the arced and ramped groove 24 depending inwardly of the circular groove 22. The circular groove 22 receives the balance 46 of the sphincterotome 12 therein.

It is a characteristic of the present invention that, when the cover 26 is detached from the mounting tray 18, at least the distal tip 14 of the sphincterotome 12 can be freely perpendicularly withdrawn from the tray 18. This prevents undesired movement of the distal tip 14 of the sphincterotome 12 during such removal. The arced and ramped groove 24 is preferably free of any conventional, inwardly depending bumps, projections or the like for otherwise retaining the distal tip 14 of the sphincterotome 12 on the mounting tray 18. However, the circular, planar groove 22 receiving the balance 46 of the sphincterotome 12 can include, and preferably does include, a plurality of conventional, inwardly depending bumps, projections or the like. Other similar means can be included for retaining the balance 46 of the sphincterotome 12 against the mounting tray 18.

Figure 4A:
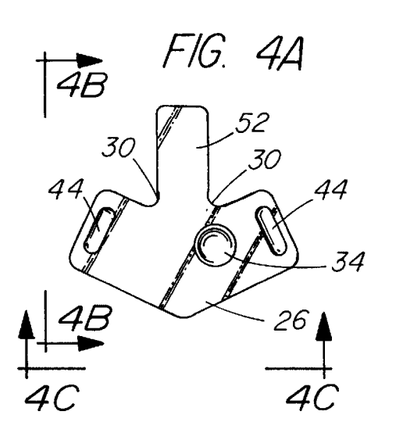
Figure 4B:
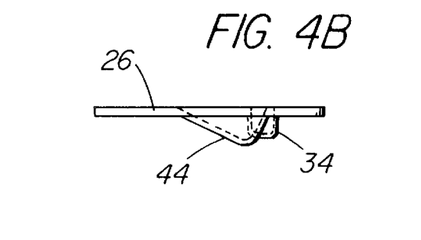
FIG. 4B is a side view taken along line 4B—4B of FIG. 4A.
Figure 4C:
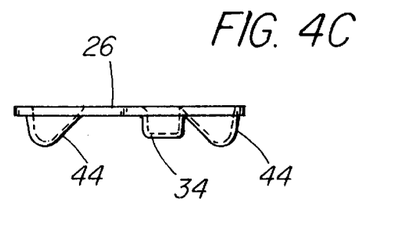
FIG. 4C is an end view taken along line 4C—4C of FIG. 4A.

The mounting tray 18 includes a recess 32 into which the distal tip 14 of the sphincterotome 12 extends. Movement of the distal tip 14 is not unrestricted in the recess, however. The cover 26 includes a plurality of projections 44 extending towards the mounting tray 18 and abutting the distal tip 14 (FIGS. 4A–4C). When the cover 26 is secured to the mounting tray 18, the projections 44 are positioned over both the recess 32 and the arced and ramped groove 24 of the tray 18. The cover 26 also includes a pair of notches 30 receiving the distal tip 14 of the sphincterotome 12 therethrough, so that the portion 28 of the distal tip 14 of the sphincterotome 12 which lies over the cover 26 extends between the notches 30. The cover 26 also includes a flat tab 52 extending from between the notches 30. The three-dimensional structure 20 of the mounting tray 18 includes an angled portion 54 on which the flat tab 52 of the cover 26 lies when the cover 26 is secured to the tray 18.

The cover 26 and the tray 18 are detachably secured to one another in any convenient manner. For example, the cover 26 and tray 18 can include one or more pairs of mating cylindrical tabs 34 and recesses 36.

Preferably, one such cylindrical tab 34 projects from the cover 26, while one such cylindrical recess 36 is formed in the tray 18.

When distal tip 14 of the sphincterotome 12 lies in the arced and ramped groove 24, securement of the cover 26 to the mounting tray 18 (with the portion 28 of the distal tip 14 lying over the cover 26) causes most of the distal tip 14 to be trapped by the projections 44 against the arced and ramped groove 24 of the mounting tray 18. In the recess 32, however, the distal tip 14 of the sphincterotome 12 instead resiliently abuts against the projections 44. Such entrapment and abutment affirmatively prevents relaxation or dislocation of the distal tip 14 during sterilization and/or storage of the sphincterotome 12.

Figure 7:
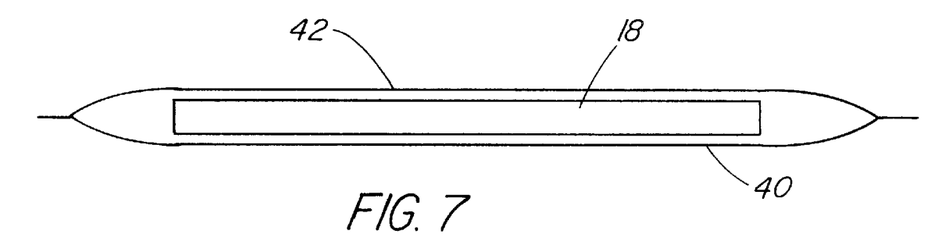
FIG. 7 is sectional view of the preferred embodiment of the present invention.

The package 10 can otherwise be configured as convenient for the sterilization and storage of the sphincterotome 12 or the like. In particular, if it is intended to sterilize the sphincterotome 12 or the like by the application of a gas such as ethylene, as shown in FIG. 7 the package 10 can further comprise a gas-permeable, medical grade backing 40 positioned adjacent to the mounting tray 18, and a transparent, medical grade polymeric sheet 42 positioned adjacent to the mounting tray 18 opposite the backing 40. The polymeric sheet 42 can be secured to the backing 40 in any convenient manner, for example, by heat-sealing or by bonding. The backing 40 can be composed of paper or TYVEK®.

Figure 6:
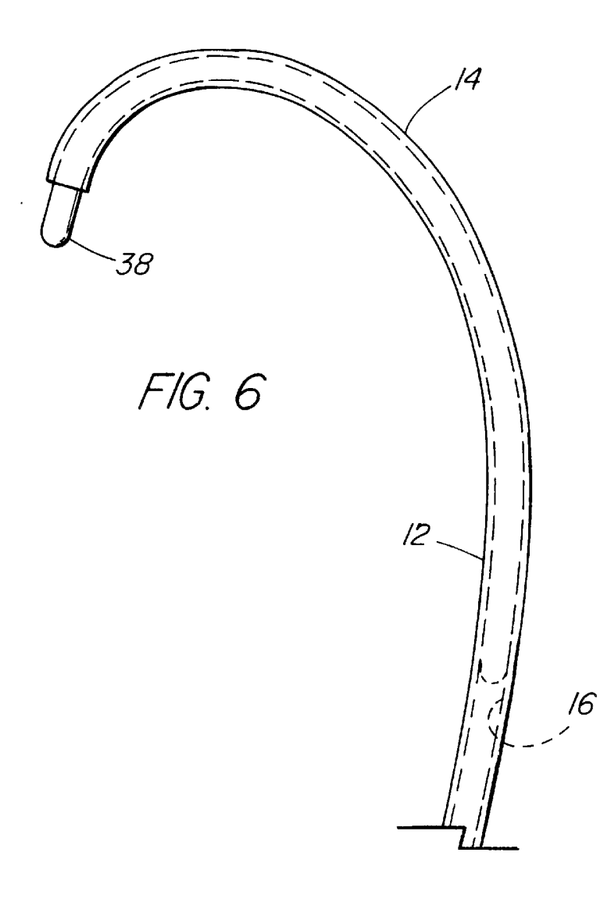
FIG. 6 is a top view of a portion of the preferred embodiment of the present invention.

Movement and relaxation of the distal tip 14 of the sphincterotome 12 or the like can further be prevented by a particularly shaped insert 38 removably received in the bore 16 in the distal tip 14 (FIG. 6). The insert 38 can be part of the package 10 described above, the package 10 thereby comprising the mounting tray 18 and the cover 26 in combination with the insert 38. Alternatively, the insert 38 can be a separate device for preventing movement and relaxation of the distal tip 14 of the sphincterotome 12, and can be employed with a generally rigid, nonrelaxing package different from that disclosed herein, or can be employed without any other rigid packaging at all. The particular material from which the insert 38 is constructed is not believed to be critical to the practice of the present invention. However, the insert 38 should be composed of a generally rigid, medical grade material more rigid than the material of the distal tip 14 of sphincterotome 12, and should be non-relaxing when subjected to the conditions of sterilization and/or storage to which the sphincterotome 12 will be subject. The insert 38 can be composed of a malleable metal or plastic material having a diameter, for example, in a range of 0.018 in. to 0.040 in., preferably 0.038 in. (0.97 mm) stainless steel wire.

Figure 5A:
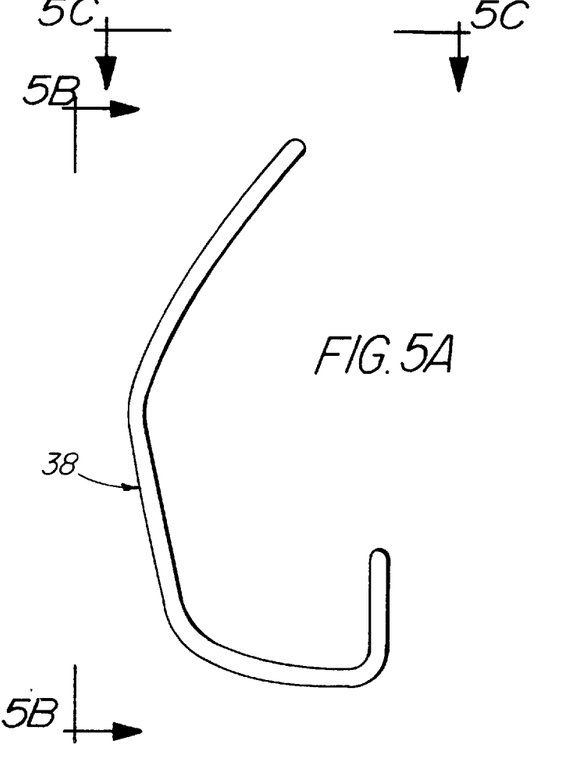
FIG. 5A is a top view of a portion of the preferred embodiment of the present invention.
Figure 5B:
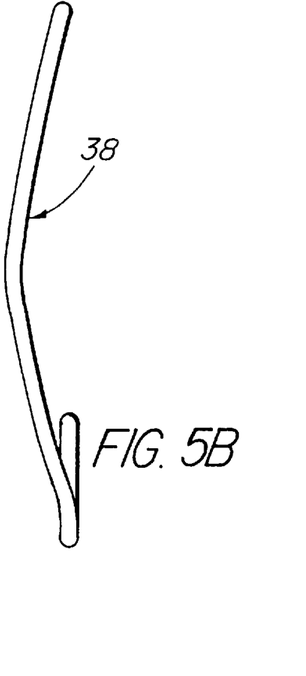
FIG. 5B is a side view taken along line 5B—5B of FIG. 5A.
Figure 5C:
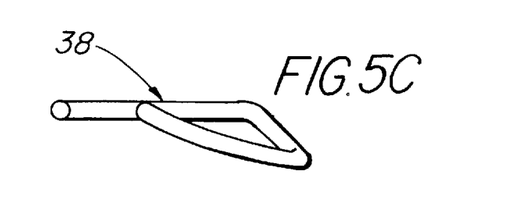
FIG. 5C is a end view taken along line 5C—5C of FIG. 5A.

In any case, the insert 38 is configured to the predetermined desired non-planar, three-dimensional shape of the distal tip 14 of the sphincterotome 12. Preferably, when incorporated in the package 10 disclosed above, the three-dimensional structure 20 of the mounting tray 18, the cover 26 and the insert 38 maintain the distal tip 14 in a shape particularly adapted for the performance of a sphincterotomy. Alternatively, when employed without the particularly disclosed package 10, the insert 38 itself maintains the distal tip 14 in a shape particularly adapted for the performance of a sphincterotomy. It is particularly preferred that the insert 38, alone or in combination with the cover 26 and the three-dimensional structure 20 of the tray 18, maintains the distal tip 14 of the sphincterotome in a 10 o'clock position with respect to the proximal balance 46 of the sphincterotome 12. The optimal shape for the insert 38, and the optimal shape in which the distal tip 14 of the sphincterotome 12 is maintained (either by the insert 38 itself, or by the combination of the insert 38, the cover 26 and the three-dimensional structure 20 of the tray 18), are substantially the shapes shown in the Figures, particularly as shown in FIGS. 5A–5C with respect to the insert 38 itself. The Figures as originally submitted are proportional representations in this regard. FIGS. 5A–5C, in particular, are intended to be full scale, proportional drawings of the insert 38. Those skilled in this art are well aware that attempting to describe in words the specific shapes of elements of medical devices is at best problematic, and at worst incomplete. Accordingly, it is believed that those skilled in this art are well capable of adequately duplicating the shapes taught in the Figures.

The present invention thus admirably provides a package for a flexible catheter, cannula, sphincterotome or the like which prevents the relaxation or change of the predetermined desired non-planar, three-dimensional shape of the distal tip of the catheter, cannula, sphincterotome or the like during sterilization and storage. The package of the present invention provides support to the predetermined desired non-planar, three-dimensional distal tip of the catheter, cannula, sphincterotome or the like throughout the entire length of that distal tip. The package of the present invention permits the perpendicular withdrawal of at least the distal tip of the catheter, cannula, sphincterotome or the like from the mounting tray without stretching that distal tip.

Any undisclosed or incidental details of the construction or composition of the various elements of the disclosed embodiment of the present invention are not believed to be critical to the achievement of the advantages of the present invention, so long as the elements possess the characteristics needed for them to perform as disclosed. The selection of these and other details of construction are believed to be well within the ability of one of even rudimentary skills in this area, in view of the present disclosure.

INDUSTRIAL APPLICABILITY

The present invention is useful in manufacturing and/or storing devices for performing surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. For use in conjunction with a flexible sphincterotome or catheter (12) having a distal tip (14) with a predetermined desired non-planar, three-dimensional shape, a package (10) preventing relaxation of the distal tip (14) of the sphincterotome or catheter (12) from its predetermined desired non-planar, three-dimensional shape, the package (10) comprising:

a generally rigid, non-relaxing mounting tray (18) with a non-planar, three-dimensional structure (20) restricting movement of at least the distal tip (14) of the sphincterotome or catheter (12); and a generally rigid, non-relaxing cover (26) detachably secured to the tray (18), trapping part and only part of the distal tip (14) of the sphincterotome or catheter (12)

against the non-planar, three-dimensional structure (20) of the tray (18), a portion (28) of the distal tip (14) of the sphincterotome or catheter (12) lying over the cover (26) opposite the tray (18);

wherein the tray (18) and cover (26) together support the distal tip (14) of the sphincterotome or catheter (12) throughout its entire length.

2. The package (10) according to claim 1, wherein the tray (18) and the cover (26) are composed of a transparent material.

3. The package (10) according to claim 1, wherein the tray (18) and the cover (26) are composed of a plastic material.

4. The package (10) according to claim 1, further comprising a gaspermeable backing (40) positioned adjacent to the tray (18).

5. The package (10) according to claim 4, wherein the backing (40) is composed of paper or TYVEK®.

6. The package (10) according to claim 4, further comprising a transparent polymeric sheet (42) positioned adjacent to the tray (18) opposite the backing (40), heat-sealed or bonded to the backing (40).

7. The package (10) according to claim 1, wherein the non-planar, three-dimensional structure (20) of the tray (18) comprises a relatively tightly arced groove (24) on which the distal tip (14) of the sphincterotome or catheter (12) lies.

8. The package (10) according to claim 7, wherein the cover (26) lies over at least part of the arced groove (24) of the tray (18).

9. The package (10) according to claim 1, wherein the non-planar, three-dimensional structure (20) of the tray (18) comprises a ramped groove (24) on which the distal tip (14) of the sphincterotome or catheter (12) lies.

10. The package (10) according to claim 9, wherein the cover (26) lies over at least part of the ramped groove (24) of the tray (18).

11. The package (10) according to claim 1, wherein the cover (26) includes a pair of notches (30) receiving the distal tip (14) of the sphincterotome or catheter (12) therethrough, the portion (28) of the distal tip (14) of the sphincterotome or catheter (12) lying over the cover (26) extending between the notches (30).

12. The package (10) according to claim 1, wherein when the cover (26) is detached from the tray (18), at least the distal tip (14) of the sphincterotome or catheter (12) can be freely perpendicularly withdrawn from the tray (18).

13. The package (10) according to claim 1, wherein the cover (26) and tray (18) are secured to one another by mating cylindrical tabs (34) and recesses (36).

14. The package (10) according to claim 1, wherein the distal tip (14) of the sphincterotome or catheter (12) includes a bore (16) defined therein, and wherein the package (10) further comprises a generally rigid, non-relaxing insert (38) removably received in the bore (16) of the distal tip (14) of the sphincterotome or catheter (12), the insert (38) being configured to the predetermined desired non-planar, three-dimensional shape of the distal tip (14) of the sphincterotome or catheter (12).

15. The package (10) according to claim 1, wherein the three-dimensional structure (20) of the tray (1 8), the cover (26) and an insert (38) maintain the distal tip (14) of the sphincterotome or catheter (12) in a shape particularly adapted for the performance of a sphincterotomy.

16. The package (10) according to claim 15, wherein the three-dimensional structure (20) of the tray (18), the cover (26) and the insert (38) maintain the distal tip (14) of the sphincterotome or catheter (12).

17. The insert (38) according to claim 14, wherin the insert (38) is particularly adapted to maintain the distal tip (14) of the sphincterotome (12) in a 10 o'clock position.

18. For use in conjunction with a flexible sphincterotome (12) having a distal tip (14) with a predetermined desired non-planar, three-dimensional shape, the distal tip (14 ) of the sphincterotome (12) including a bore (16) defined therein, a package (10) preventing relaxation of the distal tip (14) of the sphincterotome (12) from its predetermined desired non-planar, three-dimensional shape, the package (10) comprising:

a generally rigid, non-relaxing mounting tray (18) with a non-planar, three-dimensional structure (20) restricting movement of at least the distal tip (14) of the sphincterotome (12);

a generally rigid, non-relaxing cover (26) detachably secured to the tray (18), trapping part and only part of the distal tip (14) of the sphincterotome (12) against the non-planar, three-dimensional structure (20) of the tray (18), a portion (28) of the distal tip (14) of the sphincterotome (12) lying over the cover (26) opposite the tray (18); and a generally rigid, non-relaxing insert (38) removably received in the bore (16) of the distal tip (14) of the sphincterotome (1 2), the insert (38) being configured to the predetermined desired non-planar, three-dimensional shape of the distal tip (14) of the sphincterotome (12);

wherein the tray (18) and cover (26) together support the distal tip (14) of the sphincterotome (12) throughout its entire length;

wherein the non-planar, three-dimensional structure (20) of the tray (18) comprises a ramped, relatively tightly arced groove (24) on which the distal tip (14) of the sphincterotome (12) lies;

wherein the cover (26) lies over at least part of the ramped, arced groove (24) of the tray (18);

wherein the cover (26) includes a pair of notches (30) receiving the distal tip (14) of the sphincterotome (12) therethrough, the portion (28) of the distal tip (14) of the sphincterotome (12) lying over the cover (26) extending between the notches (30);

wherein when the cover (26) is detached from the tray (18), at least the distal tip (14) of the sphincterotome (12) can be freely perpendicularly withdrawn from the tray (18); and wherein the three-dimensional structure (20) of the tray (18), the cover (26) and the insert (38) maintain the distal tip (14) of the sphincterotome (12) in a shape particularly adapted for the performance of a sphincterotomy.

* * * * *